(12) United States Patent
Kohl

(10) Patent No.: US 6,410,569 B1
(45) Date of Patent: Jun. 25, 2002

(54) SALT FORM OF PANTOPRAZOLE

(75) Inventor: Bernhard Kohl, Constance (DE)

(73) Assignee: Byk Gulden Lomberg Chemische Fabrik GmbH, Constance (DE)

( * ) Notice: Subject to any disclaimer, the term of this patent is extended or adjusted under 35 U.S.C. 154(b) by 0 days.

(21) Appl. No.: 09/762,303

(22) PCT Filed: Aug. 12, 1999

(86) PCT No.: PCT/EP99/05928

§ 371 (c)(1),
(2), (4) Date: Feb. 8, 2001

(87) PCT Pub. No.: WO00/10995

PCT Pub. Date: Mar. 2, 2000

(30) Foreign Application Priority Data

Aug. 18, 1998 (DE) .......................................... 198 43 413

(51) Int. Cl.$^7$ ........................ C07D 401/12; A61K 31/44
(52) U.S. Cl. ..................................... 514/338; 546/273.7
(58) Field of Search ........................ 546/273.7; 514/338

(56) References Cited

FOREIGN PATENT DOCUMENTS

| EP | 0 166 287 | 1/1986 |
|----|-----------|--------|
| WO | 91/19710  | 12/1991 |
| WO | 92/22284  | 12/1992 |
| WO | 95/01977  | 1/1995 |
| WO | 97/41114  | 11/1997 |

*Primary Examiner*—Zinna Northington Davis
(74) *Attorney, Agent, or Firm*—Jacobson Holman, PLLC

(57) ABSTRACT

The invention relates to the dihydrate of the magnesium salt of pantoprazole.

8 Claims, No Drawings

SALT FORM OF PANTOPRAZOLE

This is a 371 of PCT/EP99/05928 filed Aug. 12, 1999.

SUBJECT OF THE INVENTION

The present invention relates to a novel salt form of the active compound pantoprazole. The novel salt form can be employed in the pharmaceutical industry for the preparation of medicaments.

PRIOR ART

Pyridin-2-ylmethylsulfinyl-1H-benzimidazoles, such as are disclosed, for example, in EP-A-0005129, EP-A-0166287, EP-A-0174726 and EP-A-0268956, have, on account of their $H^+/K^+$ ATPase-inhibiting action, considerable importance in the therapy of diseases which are due to increased gastric acid secretion. Examples of commercially available active compounds from this group are 5-methoxy-2-[(4-methoxy-3,5-dimethyl-2-pyridinyl)methylsulfinyl]-1H-benzimidazole (INN: omeprazole), 5-difluoromethoxy-2-[(3,4-dimethoxy-2-pyridinyl)methylsulfinyl]-1H-benzimidazole (INN: pantoprazole), 2-[3-methyl-4-(2,2,2-trifluoroethoxy)-2-pyridinyl)methylsulfinyl]-1H-benzimidazole (INN: lansoprazole) and 2-{[4-(3-methoxypropoxy)-3-methylpyridin-2-yl]methylsulfinyl}-1H-benzimidazole (INN: rabeprazole).

A common property of the above-mentioned pyridin-2-ylmethylsulfinyl-1H-benzimidazoles is the acid sensitivity—which is in the end indispensable for their efficacy—of these active compounds, which is seen in their strong tendency to decompose in a neutral and, in particular, acidic environment, strongly colored decomposition products being formed.

In the past, there have been considerable efforts, despite the acid sensitivity of the pyridin-2-ylmethylsulfinyl-1H-benzimidazoles, to obtain stable and storable oral administration forms which contain these pyridin-2-ylmethylsulfinyl-1H-benzimidazoles. Such stable and storable oral administration forms (e.g. tablets or capsules) are now obtainable. The preparation of these oral administration forms, however, is comparatively complicated and also certain precautions must be taken with respect to the packaging, in order that the administration forms have an adequate storage stability even under extreme storage conditions (e.g. in the tropics at high temperature and high atmospheric humidity).

The International Patent Application WO97/41114 describes a specific process for the preparation of magnesium salts of pyridin-2-ylmethylsulfinyl-1H-benzimidazoles. Inter alia, the preparation of the magnesium salt of pantoprazole is also described by way of example. According to the analysis data indicated, the salt prepared is pantoprazole magnesium in anhydrous form.

DESCRIPTION OF THE INVENTION

It has now been found that the dihydrate of the magnesium salt of pantoprazole has very surprising stability properties which make it appear to be particularly suitable for use in solid or oral administration forms. It exhibits very considerably improved stability properties both in comparison with pantoprazole itself and in comparison to pantoprazole sodium sesquihydrate (the active compound form on the market since 1994, European Patent 0 589 981), or in comparison to pantoprazole sodium monohydrate (the intermediate form used in the industrial preparations, European Patent 0 533 790).

Thus pantoprazole magnesium dihydrate is completely stable for 4 days at 90° C. and exhibits almost no discoloration or decomposition, while pantoprazole sodium sesquihydrate and mondhydrate turn brown-red in the same period with Formation of considerable amounts of decomposition products.

The invention thus relates to the dehydrate of the magnesium salt of pantoprazole (pantoprazole magnesium dihydrate).

Pantoprazole magnesium dihydrate can be employed for the treatment and prevention of all the diseases which are considered to be treatable or avoidable by the use of pyridin-2-ylmethylsulfinyl-1H-benzimidazoles. In particular, pantoprazole magnesium dihydrate can be employed in the treatment of disorders of the stomach.

On account of its solubility properties, possibilities of application for pantoprazole magnesium dihydrate are conceivable for whose realization resort had to be made up to now to particular pharmaceutical preparations. Thus use of pantoprazole magnesium dihydrate is particularly suitable, inter alia, where the active compound is to be released and absorbed over a relatively long period (see, for example, European Patent Application 0 841 903). By means of a combination of the magnesium salt of pantoprazole with the sodium salt, a solution made to order for certain desired active compound blood level courses can be achieved.

The pantoprazole magnesium dehydrate is prepared in a manner known per se by reaction of pantoprazole or a readily soluble pantoprazole salt (e.g. pantoprazole sodium) with a magnesium salt in water or in mixtures of water with polar organic solvents (e.g. alcohols, preferably ethanol or isopropanol, or ketones, for example acetone or butanone).

Suitable magnesium salts which can be employed according to the process are, for example, magnesium chloride, bromide, fluoride, iodide, formate, acetate, propionate, sulfate, gluconate or carbonate. Alkoxides of magnesium (e.g. magnesium methoxide, ethoxide, (iso)propoxide, butoxide, hexoxide or phenoxide), or magnesium hydroxide can also be reacted with pantoprazole or pantoprazole sodium in aqueous medium.

EXAMPLE

Magnesium bis[5-[difluoromethoxy]-2-[[3,4-dimethoxy-2-pyridinyl]methyl]sulfinyl]-1H-benzimidazolide]dihydrate 3.85 kg (8.9 mol) of pantoprazole Na sesquihydrate [sodium [5-[difluoromethoxy]-2-[[3,4-dimethoxy-2-pyridinyl]methyl]sulfinyl]-1H-benzimidazolide] sesquihydrate] are dissolved at 20–25° C. in 38.5 l of purified water in a stirring vessel. A solution of 1.0 kg (4.90 mol) of magnesium dichloride hexahydrate in 8 l of purified water is added with stirring at 20–30° C. in the course of 3 to 4 h. After stirring for a further 18 h, the precipitated solid is centrifuged, washed with 23 l of purified water, stirred at 20–30° C. for 1 to 2 h in 35 l of purified water, centrifuged again and washed again with 30–50 l of purified water. The solid product is dried at 50° C. in vacuo (30–50 mbar) until a residual water content of <4.8% is achieved. The product is then ground.

The title compound is obtained as a white to beige powder, which is employed directly for further pharmaceutical processing.

Yield: 3.40 kg (90% of theory); water content: 4.5–4.6%; melting point: 194–196° C. with decomposition.

| CHN analysis | C | H | N | S |
| --- | --- | --- | --- | --- |
| Theory | 46.58 | 3.91 | 10.19 | 7.77 |
| Found | 46.33 | 3.89 | 10.04 | 7.83 |

Alternatively the title compound can be produced using mixtures of organic solvents with water. For this, pantoprazole Na sesquihydrate is dissolved in an organic solvent at 50–60° C. 0.5 mole equivalents of the magnesium salt (e. g. magnesium chloride hexahydrate), dissolved in water, are added drop by drop and the solution is allowed to cool with stirring. The precipitated solid is filtered off, washed with the corresponding organic solvent and is dried in vacuo at 50° C. to constant weight. The title compound is obtained as a colourless powder. Examples for different solvents are given in the following table 1.

TABLE 1

| pantoprazole Na sesquihydrate | organic solvent | water | yield of title compound | melting point ° C. | water content % |
| --- | --- | --- | --- | --- | --- |
| 50 g | isopropanol 300 ml | 300 ml | 45,4 g | 196–197 | 4,4–4,5 |
| 50 g | isopropanol 300 ml | 120 ml | 45,9 g | 196–197 | 4,3 |
| 50 g | ethanol 300 ml | 300 ml | 45,8 g | 197–198 | 4,6 |
| 50 g | acetone 300 ml | 300 ml | 45,6 g | 195–196 | 4,6–4,7 |

Alternatively the title compound can be produced by reacting pantoprazole with a basic magnesium salt, such as magnesium methylate, for example in the following manner: 90 g of pantoprazole are dissolved in 700 ml of 2-propanol at 60–70° C. 13.4 g (0.5 moles) of solid magnesium methylate are added, the solution is allowed to cool with stirring and filtered. After addition of 36 ml of water the crystalline solid formed is filtered off, washed with water and dried in vacuo at 50° C. to constant weight. The title compound of melting point 194–196° C. (water content 4.8%) is obtained as beige solid.

What is claimed is:

1. A compound pantoprazole magnesium dihydrate.
2. A medicament composition comprising the compound of claim 1 together with a customary auxiliary.
3. A pharmaceutical composition comprising a combinatio of the compound of claim 1 and pantoprazole sodium sesquihydrate.
4. The compound of claim 1 and pantoprazole sodium sesquihydrate in the weight ratio (based on pantoprazole) of 10% pantoprazole magnesium dihydrate and 90% pantoprazole sodium sesquihydrate to 90% pantoprazole magnesium dihydrate and 10% pantoprazole sodium sesquihydrate.
5. The compound of claim 1 and pantoprazole sodium sesquihydrate in the weight ratio (based on pantoprazole) of 25% pantoprazole magnesium dihydrate and 75% pantoprazole sodium sesquihydrate to 75% pantoprazole magnesium dihydrate and 25% pantoprazole sodium sesquihydrate.
6. The compound of claim 1 and pantoprazole sodium sesquihydrate in the weight ratio (based on pantoprazole) of 40% pantoprazole magnesium dihydrate and 60% pantoprazole sodium sesquihydrate to 60% pantoprazole magnesium dihydrate and 40% pantoprazole sodium sesquihydrate.
7. The compound of claim 1 and pantoprazole sodium sesquihydrate in the weight ratio (based on pantoprazole) of 50% pantoprazole magnesium dihydrate and 50% pantoprazole sodium sesquihydrate.
8. A method of treating an amenable disorder of the stomach or intestine which comprises administering an effective amount of the compound of claim 1 to a subject in need of such therapy.

* * * * *

UNITED STATES PATENT AND TRADEMARK OFFICE
CERTIFICATE OF CORRECTION

PATENT NO. : 6,410,569 B1 Page 1 of 1
DATED : July 25, 2002
INVENTOR(S) : Kohl

It is certified that error appears in the above-identified patent and that said Letters Patent is hereby corrected as shown below:

<u>Column 4,</u>
Line 9, please delete the term "medicament" and replace it with the term
-- pharmaceutical --.
Lines 11-12, please delete the term "combinatio" and replace it with the term
-- combination --.
Lines 14, 19, 24 and 29, please delete the term "The" and replace it with the following
-- A pharmaceutical composition comprising a combination of the --.

Signed and Sealed this

Fourth Day of January, 2005

JON W. DUDAS
*Director of the United States Patent and Trademark Office*